US00PP23418P2

(12) United States Plant Patent
Plunkett

(10) Patent No.: US PP23,418 P2
(45) Date of Patent: Feb. 26, 2013

(54) APPLE TREE NAMED 'PLUMAC'

(50) Latin Name: *Malus domestica*
Varietal Denomination: PLUMAC

(76) Inventor: Geoffrey R. P. Plunkett, Upper Moutere (NZ)

( * ) Notice: Subject to any disclaimer, the term of this patent is extended or adjusted under 35 U.S.C. 154(b) by 203 days.

(21) Appl. No.: 13/065,627

(22) Filed: Mar. 25, 2011

Related U.S. Application Data

(60) Provisional application No. 61/343,787, filed on May 4, 2010.

(51) Int. Cl.
*A01H 5/00* (2006.01)

(52) U.S. Cl. ..... Plt./161

(58) Field of Classification Search ..... Plt./161
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of apple tree, 'PLUMAC' that is characterized by having a tree habit that is weeping and naturally feathering allowing the tree to be easily trained, tree bark that is greyed orange in color, and fruit that is mottled, flushed and striped, has excellent pressure and texture with a very sweet flavor, is late in coloring and has a long harvest season, is large in size with the large size developing evenly throughout the tree, and that stores well in a coolstore without problems such as bitter pit, scald, water core, or discoloration.

3 Drawing Sheets

Botanical classification: *Malus domestica.*
Varietal denomination: 'PLUMAC'.

BACKGROUND OF THE INVENTION

The present invention relates to a new and distinct cultivar of apple tree, botanically known as *Malus domestica* 'PLUMAC', referred to hereafter by its cultivar name, 'PLUMAC'.

The new cultivar, 'PLUMAC', was discovered as a chance seedling in 1998 by the Inventor in a garden in Upper Moutere, Nelson, New Zealand. The parentage is unknown. The cultivars 'Fuji' (not patented) and 'Braeburn' (not patented) are probable parents based on their characteristics and their proximity to the new cultivar in the area of discovery.

Asexual reproduction of the new cultivar was first accomplished by means of budding onto M9 rootstock under the direction of the Inventor in Waikato, New Zealand in 2002. The asexually propagated trees of 'PLUMAC' have been determined to be stable and are reproduced true to type in successive generations.

SUMMARY OF THE INVENTION

The following traits have been repeatedly observed and represent the characteristics of the new cultivar. The measurements, observations and descriptions that follow describe plants grown outdoors and observed for six years in Waikato, New Zealand.

1. 'PLUMAC' exhibits a tree habit that is weeping and naturally feathering allowing the tree to be easily trained.
2. 'PLUMAC' exhibits fruit with skin that is mottled, flushed and striped with an orange tinge.
3. 'PLUMAC' exhibits tree bark that is greyed orange in color.
4. 'PLUMAC' exhibits fruit that has excellent pressure and texture with a very sweet flavor.

5. 'PLUMAC' exhibits fruit that stores well in a coolstore without problems such as bitter pit, scald, water core, or discoloration.
6. 'PLUMAC' exhibits fruit that is late in coloring and has a long harvest season.
7. 'PLUMAC' exhibits fruit that is large in size and that evenly develop throughout the tree.

'PLUMAC' can be readily distinguished from its probable parent plants, 'Fuji' and 'Braeburn'. 'PLUMAC' differs from 'Fuji' in having a weeping habit rather than a spreading habit, in having fruit that can be harvested 20 days earlier, in having slower fruit oxidation, and in lacking the fruit storage problems of water core and discoloration that can be observed with 'Fuji'. 'PLUMAC' differs from 'Braeburn' in having a weeping habit rather than an upright and spreading habit, in having fruit that is sweeter and that can be harvested 10 days earlier, and in lacking the fruit storage problems of bitter pit that can be observed with 'Braeburn'. 'PLUMAC' can also be compared to the cultivar 'Scifresh' (U.S. Plant Pat. No. 13,888). 'PLUMAC' differs from 'Scifresh' in having a weeping habit rather than a spreading habit, in having fruit that are larger in size, stripes that are more red in color, more rounded in shape, sweeter in taste at maturity. The fruit can also be harvested 7 days earlier and in lacks the storage problem of scald that is often observed with 'Scifresh'.

Table 1 provides a summary of fruit characteristics recorded on mature fruit for 'PLUMAC' in comparison to 'Fuji' for two seasons and in comparison to 'Braeburn', and 'Scifresh' for three seasons. Data is presented for background color, starch pattern index, flesh firmness, and soluble solids (% Brix).

TABLE 1

| Maturity data summary | | | | |
|---|---|---|---|---|
| Variety | Background colour (Fuji Swatch) | Starch pattern index (0-6) | Flesh Firmness (kg-f) | Soluble Solids % Brix |
| 17 Mar. 2007 | | | | |
| Plumac | 5.4 | 3.2 | 8.6 | 14.4 |
| Braeburn | 3.5 | 1.2 | 9.2 | 11.3 |
| Fuji | 2.6 | 1.5 | 8.3 | 12.3 |
| Scifresh | 5.1 | 2.5 | 9.2 | 13.1 |
| 24 Mar. 2007 | | | | |
| Plumac | 5.7 | 4.2 | 8.3 | 14.7 |
| Braeburn | 3.2 | 1.0 | 9.4 | 11.1 |
| Fuji | 3.2 | 1.3 | 8.1 | 12.5 |
| Scifresh | 3.8 | 2.5 | 9.4 | 13.0 |
| 17 Mar. 2008 | | | | |
| Plumac | 3.6 | 3.0 | 8.3 | 12.7 |
| Braeburn | 2.9 | 0.8 | 8.7 | 11.2 |
| Fuji | 3.1 | 1.8 | 7.9 | 12.6 |
| Scifresh | 4.3 | 1.8 | 8.9 | 13.0 |
| 24 Mar. 2008 | | | | |
| Plumac | 3.6 | 4.1 | 8.3 | 13.0 |
| Braeburn | 3.0 | 1.1 | 8.9 | 11.2 |
| Fuji | 3.0 | 2.3 | 8.4 | 12.7 |
| Scifresh | 4.4 | 3.1 | 9.1 | 13.3 |
| 17 Mar. 2009 | | | | |
| Plumac | 6.3 | 4.6 | 9.3 | 14.6 |
| Braeburn | 3.4 | 0.5 | 9.2 | 11.0 |
| Scifresh | 4.6 | 1.8 | 9.3 | 12.5 |

[1]Average values for harvests on 17th and 24th March in each year, at least 20 fruit samples per cultivar per harvest Nelson region, New Zealand

BRIEF DESCRIPTION OF THE DRAWINGS

The accompanying color photographs illustrate the distinguishing characteristics of the new cultivar, 'PLUMAC', as grown in an orchard in Waikato, New Zealand. The photographs were taken of a plant 4 years in age as grown on M9 rootstock. The colors in the photographs are as close as possible with the digital photography and printing techniques utilized and the color codes in the detailed botanical description more accurately describe the new apple tree.

DETAILED BOTANICAL DESCRIPTION

Figure 1:
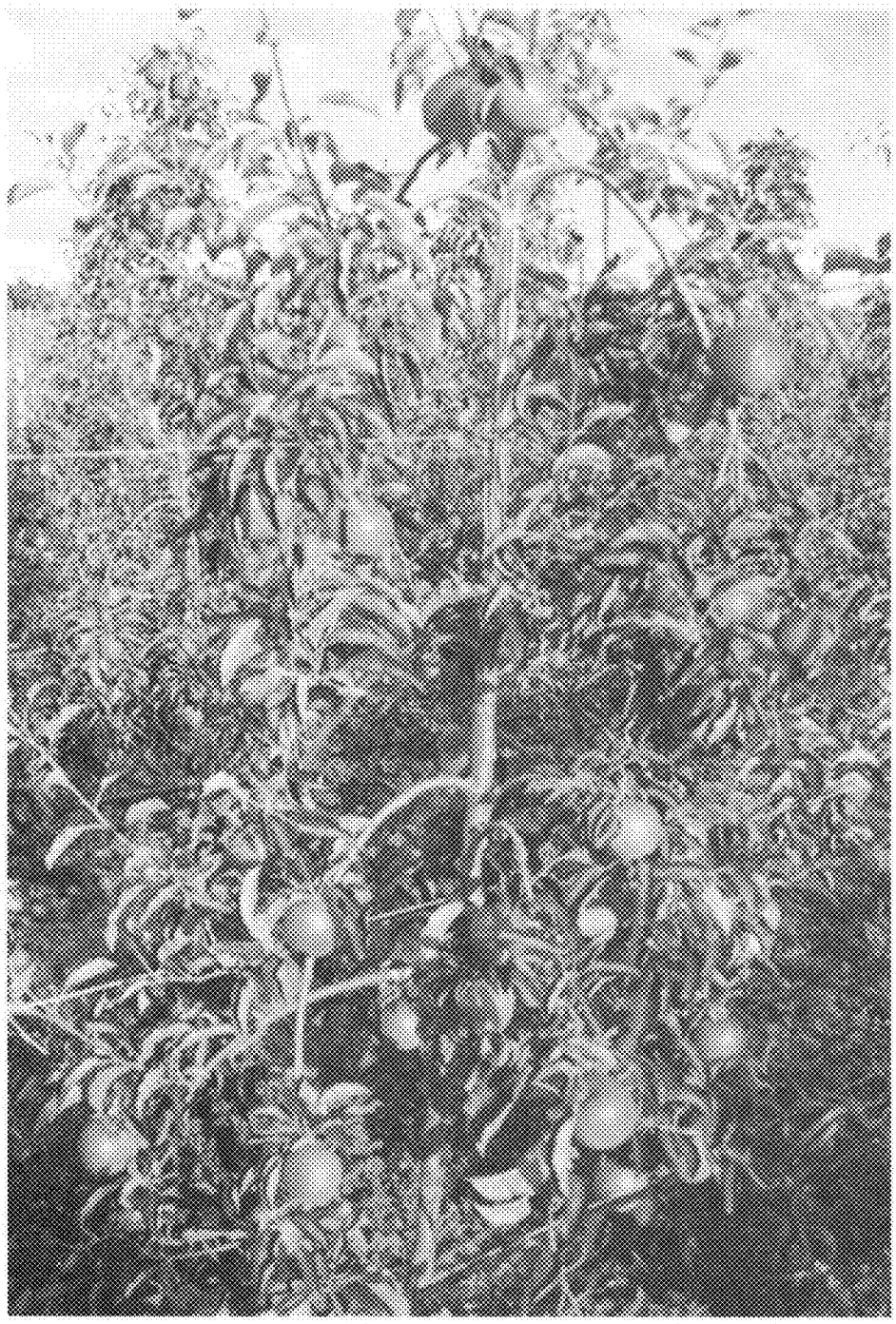
FIG. 1 shows a tree of 'PLUMAC' and illustrates its weeping branches and crop development prior to harvest.
Figure 2:
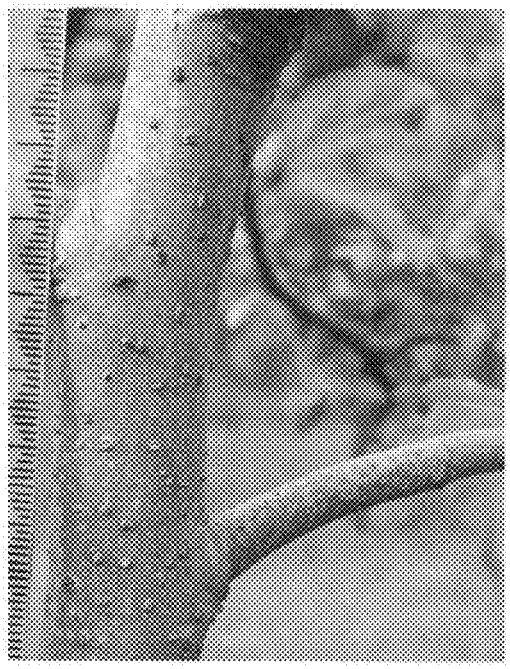
FIG. 2 shows a trunk of 'PLUMAC' and illustrates the lenticels and distinct greyed orange coloration of the bark.
Figure 3:
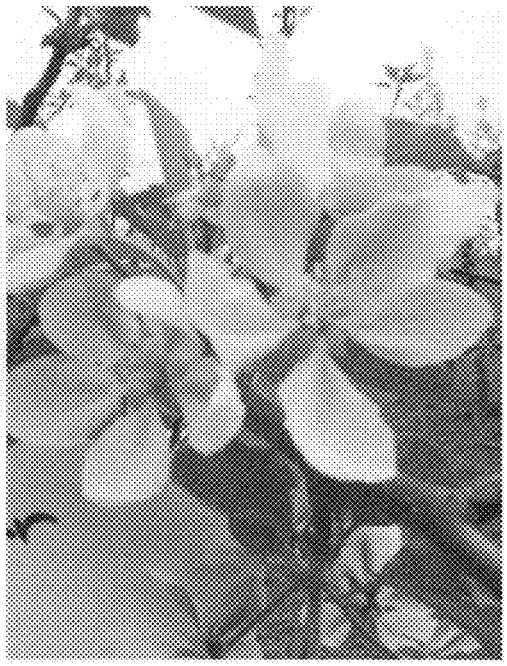
FIG. 3 provides a close-up view of the flowers of 'PLUMAC'.
Figure 4:
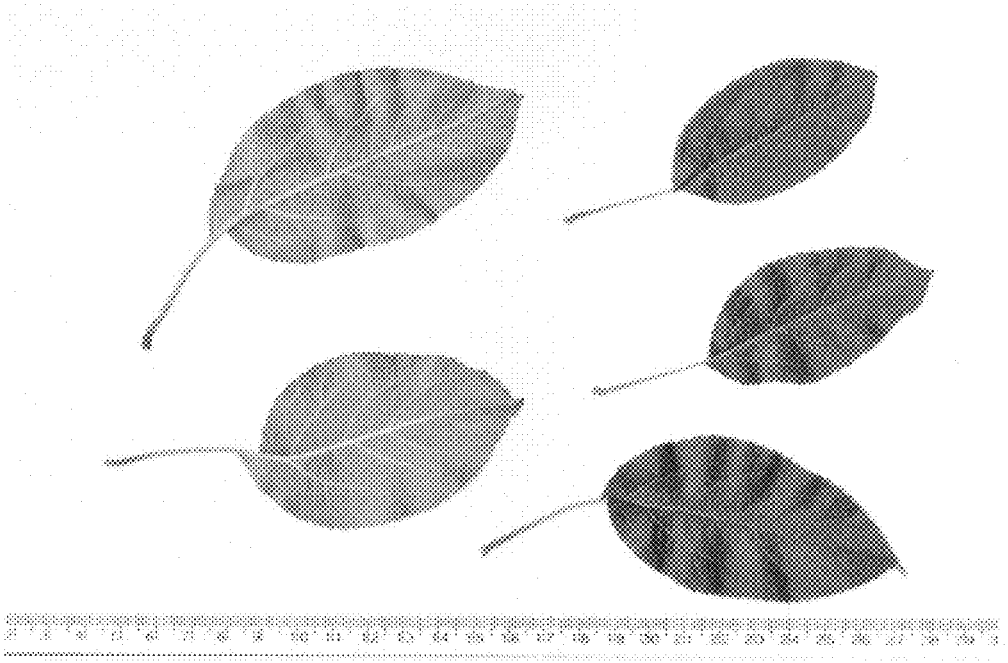
FIG. 4 provides a close-up view of the leaves of 'PLUMAC' with the lower surface of the leaves shown on the left and the upper surface of the leaves shown on the right.
Figure 5:
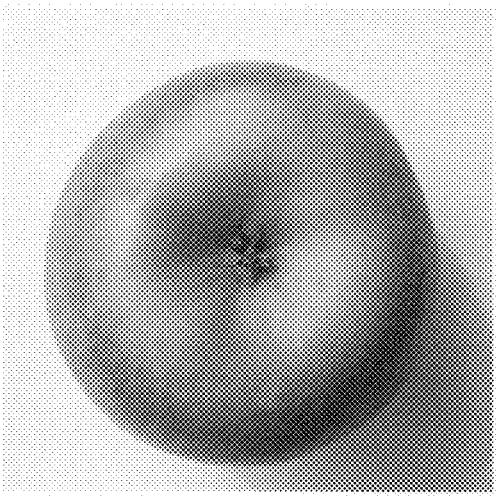
FIG. 5 provides a view of the calyx end of the fruit of 'PLUMAC'.
Figure 6:
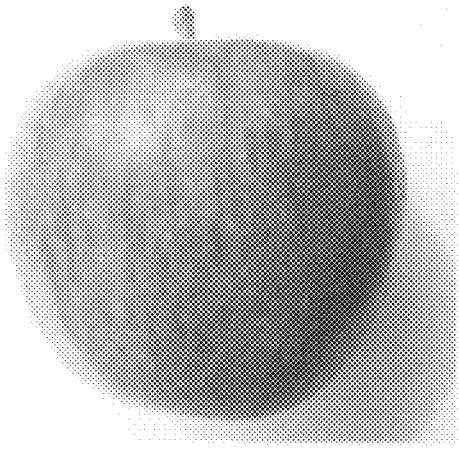
FIG. 6 provides a side view of a typical fruit of 'PLUMAC'.
Figure 7:
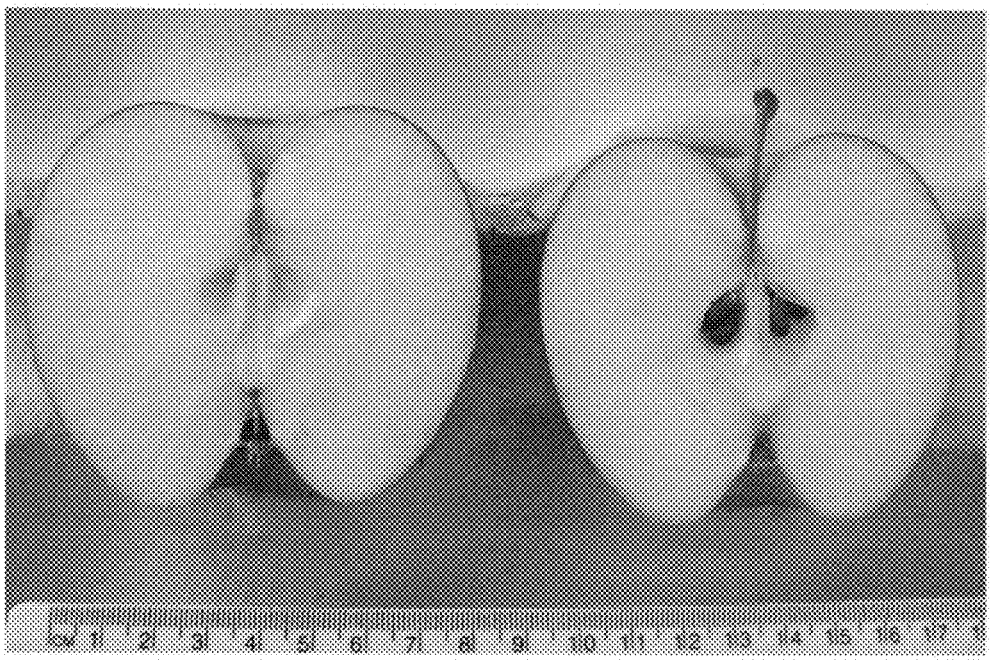
FIG. 7 provides a cross sectional view of a typical fruit of 'PLUMAC'.

The following is a detailed description of four year-old plants of the new apple variety budded onto M9 rootstock and grown in the field under standard orchard management in Waikato, New Zealand. 'PLUMAC' has not been observed under all possible environmental conditions. The phenotype may vary somewhat with variations in temperature, day length, light intensity, soil types and water and fertility levels, without, however, any variance in the genotype. The color determination is in accordance with The 2001 R.H.S. Colour Chart of The Royal Horticultural Society, London, England, except where general color terms of ordinary dictionary significance are used.

Tree description:

*Tree habit*.—Drooping to weeping and naturally feathered.

*Tree size*.—Approximately 2.4 m in height and 1.4 m in width at 1 m above graft union.

*Vigor*.—Medium to strong.

*Diseases resistance*.—Some resistance to blackspot has been shown in field observations.

*Hardiness*.—Has been observed to grow and crop well from Waikato, New Zealand (Latitute 37° 47'S) to Central Otago, New Zealand (Latitute 45° 33'S).

*Branching habit*.—Weeping.

*Branch frequency*.—High.

*Branch strength*.—Strong.

*Angle of bearing branches*.—Approximately 20° above horizontal from tree trunk, then branches droop below horizontal.

*Bark of tree trunk*.—166B in color, medium roughness, lenticels; raised, 1.5 to 2 mm in length, 1 mm in width, 156C in color.

Description of dormant shoots:

*Stem appearance*.—Moderately rough, slightly pubescent near new leaves.

*Stem strength*.—Strong.

*Thickness of shoot at center of middle internode*.—Ranging from 4 to 6 mm in width.

*Shine of bark*.—Weak to medium.

*Stem pubescence*.—Weak on main stem, medium pubescence near new growing tip.

*Stem color*.—177A.

*Lenticels*.—Round to oval in shape, N155D in color, 6 to 12 per sq. cm.

Description of growing shoots:

*Color of growing tip of shoot*.—156D with anthocyanin 178A.

*Shoot tip leaves in cross section*.—Concave in shape, pubescent, 144A in color.

*Distribution of color other than green on shoot tips leaves*.—Overlay of 59B.

Leaf description:

*Leaf orientation*.—Upward.

*Leaf division*.—Simple.

*Leaf shape*.—Ovate or oval.

*Leaf blade size*.—Average of 7.6 cm in length and 3.7 cm in width.

*Leaf apex*.—Cuspidate.

*Leaf base*.—Obtuse to oblique.

*Leaf surface*.—Glossy on upper surface, slightly pubescent on lower surface.

*Leaf margin*.—Serrate.

*Leaf color*.—Upper surface emerging leaves; 144A, lower surface emerging leaves 137C, mature leaves upper surface 139A, mature leaves lower surface 138A.

*Leaf anthocyanin color on margin*.—Emerging leaves 59B, mature leaves 181A.

*Leaf venation*.—Pinnate main veins with netted minor veins, upper surface 145B in color, lower surface 157B in color.

*Petiole size*.—Average of 2.75 cm in length, 1.5 mm in diameter.

*Petiole color*.—145C and 59B on base.

*Petiole surface*.—Smooth with slight pubescence at base.

*Durability of foliage to stress*.—Leaves become more concave with stress.

*Stipules*.—Average 8 mm in length on newly developed leaves, 59B in color.

Flower description:

*Flowering period*.—Mid-season.

*Beginning flowering date*.—Typically about September 30th in Waikato, New Zealand.

*Ending flowering date*.—Petal senescence is typically about October 24$^{th}$ in Waikato, New Zealand.

*Number of flowers*.—Average of 5 per cluster.

*Inflorescence type*.—Corymb.

*Flower buds*.—Round in shape, 63A in color at pink tip stage, average of 1.1 cm in length and 8 mm in diameter.

*Flower size*.—Average of 4 cm in diameter, 1.3 cm in depth.

*Flower fragrance*.—Mild.

*Flower aspect*.—Upright.

*Petals*.—5 per flower, un-fused, margins of petals not touching, ovate in shape, rounded obtuse apex, round base, entire margin, about 1.6 cm in length and 9.5 mm in width, color of upper surface is 155C with veins 70B, color of lower surface is 155C with strong overcolor of 70B on the mid-veins and throughout petal.

*Sepals*.—5 per flower, 143C in color with tips 59B (upper and lower surface), slightly pubescent, triangular in shape, entire margin, acute reflexed apex, fused base, average of 5 mm in length and 3 mm in width.

*Pedicel*.—144A in color, average of 1.7 cm in length and 1.5 mm in width, surface is smooth.

*Pistil*.—Compound carpel with 5 stigmas fused at base, 10.5 mm in length, style is 3B in color and 7 mm in length, stigma is 150C in color, ovary is pubescent and N155C to 155B in color.

*Stamens*.—About 20 per flower, anther is oblong in shape, 10C in color and 1.5 mm in length, pollen is 10A in color and moderate in abundance.

Fruit description:

*Fruit size*.—Medium to large, 7.3 to 7.9 cm in diameter, 6.4 to 7.6 cm in height, average of 211 g in weight.

*Position of maximum diameter*.—Above midway between proximal and distal ends.

*Fruit shape*.—Globose conical.

*Fruit symmetry*.—Slightly asymmetric.

*Fruit ribbing*.—Absent, slightly crowning at calyx end.

*Fruit aperture of eye*.—Closed.

*Size of eye*.—Average of 8.5 mm in diameter.

*Persistence of calyx*.—Persistent at harvest.

*Sepal*.—Average 6 mm in length, slightly pubescent, 146D in color.

*Spacing of sepals at base*.—Touching to overlapping.

*Depth of eye basin*.—Mean 15 mm, range 13 to 20 mm.

*Width of eye basin*.—Mean 31 mm, range 28 to 34 mm.

*Thickness of stalk*.—Mean 2.7 mm, range 2.5 to 3.0 mm.

*Color of stalk*.—164A and slightly greener than 160A on shaded side.

*Length of stalk*.—Mean 24 mm, range 17 to 37 mm.

*Depth of stalk cavity*.—Mean 17 mm, range 12 to 21 mm.

*Width of stalk cavity*.—Mean 31 mm, range 25 to 33 mm.

*Relief of surface*.—Smooth.

*Cracking tendency of skin*.—Absent.

*Bloom of skin*.—None.

*Waxiness of skin*.—Not present at harvest.

*Thickness of skin*.—Medium.

*Skin color*.—Flushed, striped and mottled, base color is 1C to 1D, mottled over 85 to 95% with 47A over 70-85% of fruit, weakly striped with 46A.

*Presence of russet*.—Small amount present around stalk and calyx cavity.

*Lenticels*.—Small (<1.0 mm), circular, density increasing towards calyx, slightly prominent to slight depressed.

*Color of flesh*.—159D.

*Distinctness of core line*.—Low to medium, transverse cross section vascular bundles distinct.

*Aperture of locules*.—Closed, carpels; ovate in shape, smooth, an average of 10 mm in length and 4 mm in width.

*Fruit set*.—Good.

*Fruit bearing habit*.—Annually on spurs and long shoots.

*Fruit maturity date*.—Medium season, harvest season is about March 5th to March 30th in Waikato, New Zealand.

*Seed*.—Ovoid to deltoid in shape, 1 to 2 seeds per chamber, average of 7 seeds per fruit, average of 8.7 mm in length, 3.9 mm in width and 2.5 mm in depth, color is N170A at base and 166B at apex.

*Browning of flesh*.—Weak, resistant to oxidation.

*Fruit flavor*.—Sweet.

*Firmness* (*without skin*).—8.7 kgf, 7.5 kgf after 120 days in refrigerated air storage (1° C.).

*Texture of flesh*.—Crisp and juicy.

*Acidity*.—0.37% titratable acidity (malic acid equivalent).

*Brix*.—13.1%, 14.7% after 120 days in refrigerated air storage (1° C.). High temperature tolerance: Average. Low temperature tolerance: Average.

*Storage life*.—Not susceptible to storage disorders such as bitter pit, scald, water core, or discoloration, retains quality for 4 to 5 months in air storage and significantly longer in Controlled Atmosphere.

It is claimed:

1. A new and distinct variety of apple tree named 'PLUMAC' as described and illustrated herein.

* * * * *